US008740857B2

(12) United States Patent
Christiansen et al.

(10) Patent No.: US 8,740,857 B2
(45) Date of Patent: Jun. 3, 2014

(54) SYRINGE DEVICE

(75) Inventors: Asger Voss Christiansen, Guldborg (DK); Jonas Torry-Smith, Copenhagen V (DK); Michael Ejstrup Hansen, Morud (DK); Nikolaj Eusebius Jakobsen, Valby (DK); Ramin Nateghi Elahi, Gørløse (DK); Claus Schmidt Møller, Fredensborg (DK); Claus Urup Gjødesen, Copenhagen Ø (DK)

(73) Assignee: Novo Nordisk A/S, Bagsvaerd (DK)

( * ) Notice: Subject to any disclaimer, the term of this patent is extended or adjusted under 35 U.S.C. 154(b) by 890 days.

(21) Appl. No.: 12/518,502

(22) PCT Filed: Dec. 21, 2007

(86) PCT No.: PCT/EP2007/064525
§ 371 (c)(1),
(2), (4) Date: Oct. 23, 2009

(87) PCT Pub. No.: WO2008/074897
PCT Pub. Date: Jun. 26, 2008

(65) Prior Publication Data
US 2010/0106099 A1    Apr. 29, 2010

Related U.S. Application Data

(60) Provisional application No. 60/899,057, filed on Feb. 2, 2007.

(30) Foreign Application Priority Data

Dec. 21, 2006 (EP) ..................................... 06026567

(51) Int. Cl.
A61M 5/00    (2006.01)

(52) U.S. Cl.
USPC ........................................... 604/232; 604/208

(58) Field of Classification Search
USPC .................. 604/207, 208, 209, 210, 211, 232
See application file for complete search history.

(56) References Cited

U.S. PATENT DOCUMENTS 31,873 A    4/1861  Cramer
31,878 A    4/1861  Downer
(Continued)

FOREIGN PATENT DOCUMENTS

CH    0315980    9/1956
CH    0501411    1/1971
(Continued)

OTHER PUBLICATIONS

English language abstract for CH0315980.
(Continued)

Primary Examiner — Kevin C. Sirmons
Assistant Examiner — William Carpenter
(74) Attorney, Agent, or Firm — Wesley A. Nicolas; Marc A. Began; Reza Green

(57) ABSTRACT

A medical delivery system comprising a container and a coupling mechanism movable between a coupling position wherein distal movement of a drive mechanism is transferred to an actuator, and a non-coupling position wherein distal movement is not transferred to the actuator. Moreover the present invention relates to a dosing assembly for use in the medical delivery system and a container for use in the medical delivery system. Finally, the present invention relates to medical delivery system comprising a dosing assembly having means for preventing a drive stem of the dosing assembly from being moved in a distal direction.

14 Claims, 7 Drawing Sheets

(56) References Cited

U.S. PATENT DOCUMENTS

| | | | |
|---|---|---|---|
| 1,594,493 A | 8/1926 | Brown | |
| 2,020,828 A | 11/1935 | Goldberg | |
| 2,707,466 A | 5/1955 | Hoskins | |
| 2,818,864 A | 1/1958 | Hudson | |
| 2,865,372 A | 12/1958 | Miskel et al. | |
| 2,880,723 A | 4/1959 | Adams | |
| 2,888,924 A | 6/1959 | Dunmire | |
| 3,021,840 A | 2/1962 | Hallamore et al. | |
| 3,130,724 A | 4/1964 | Higgins et al. | |
| 3,130,742 A | 4/1964 | Higgins et al. | |
| 3,170,667 A | 2/1965 | Szohatzky | |
| 3,336,924 A | 8/1967 | Sarnoff et al. | |
| 3,375,825 A | 4/1968 | Keller | |
| 3,820,652 A | 6/1974 | Tiiackston | |
| 3,831,599 A | 8/1974 | Needham | |
| 3,895,633 A | 7/1975 | Bertner et al. | |
| 3,916,893 A | 11/1975 | De Felice | |
| 3,989,044 A | 11/1976 | Meierhoefer | |
| 4,089,432 A | 5/1978 | Crankshaw | |
| 4,150,673 A | 4/1979 | Watt | |
| 4,280,723 A | 7/1981 | Moldestad | |
| 4,490,142 A | 12/1984 | Silvern | |
| 4,592,745 A | 6/1986 | Rex et al. | |
| 4,619,640 A | 10/1986 | Potolsky et al. | |
| 4,619,651 A | 10/1986 | Kopfer et al. | |
| 4,664,656 A | 5/1987 | Taddei | |
| 4,685,314 A | 8/1987 | Greenwalt et al. | |
| 4,693,833 A | 9/1987 | Toshikuni et al. | |
| 4,740,205 A | 4/1988 | Seltzer | |
| 4,768,568 A | 9/1988 | Fournier et al. | |
| 4,781,701 A | 11/1988 | Geprags | |
| 4,865,591 A * | 9/1989 | Sams | 604/186 |
| 4,936,833 A * | 6/1990 | Sams | 604/232 |
| 4,944,736 A | 7/1990 | Holtz | |
| 4,948,000 A | 8/1990 | Grabenkort | |
| 4,973,318 A * | 11/1990 | Holm et al. | 604/208 |
| 4,976,701 A | 12/1990 | Ejlersen et al. | |
| 5,000,744 A | 3/1991 | Hoffman et al. | |
| 5,002,537 A | 3/1991 | Hoffman et al. | |
| 5,017,190 A | 5/1991 | Simon et al. | |
| 5,084,017 A | 1/1992 | Maffetone | |
| 5,205,833 A | 4/1993 | Harsh et al. | |
| 5,226,896 A | 7/1993 | Harris | |
| 5,244,465 A | 9/1993 | Michel | |
| 5,269,317 A | 12/1993 | Bennett | |
| 5,279,585 A * | 1/1994 | Balkwill | 604/207 |
| 5,286,258 A | 2/1994 | Haber et al. | |
| 5,458,580 A | 10/1995 | Hajishoreh | |
| 5,478,323 A | 12/1995 | Westwood et al. | |
| 5,498,253 A | 3/1996 | Bonnichsen | |
| 5,554,134 A | 9/1996 | Bonnichsen | |
| 5,584,815 A | 12/1996 | Pawelka et al. | |
| 5,611,783 A * | 3/1997 | Mikkelsen | 604/208 |
| 5,688,251 A * | 11/1997 | Chanoch | 604/208 |
| 5,693,027 A | 12/1997 | Hansen et al. | |
| 5,743,889 A * | 4/1998 | Sams | 604/211 |
| 5,938,642 A * | 8/1999 | Burroughs et al. | 604/208 |
| 5,954,700 A | 9/1999 | Kovelman | |
| 5,957,896 A * | 9/1999 | Bendek et al. | 604/207 |
| 6,017,330 A | 1/2000 | Hitchins et al. | |
| 6,197,040 B1 | 3/2001 | Lavaughn et al. | |
| 6,221,046 B1 * | 4/2001 | Burroughs et al. | 604/153 |
| 6,582,399 B1 | 6/2003 | Smith et al. | |
| 6,582,408 B1 | 6/2003 | Buch-Rasmussen et al. | |
| 6,648,859 B2 | 11/2003 | Bitdinger et al. | |
| 7,195,616 B2 * | 3/2007 | Diller et al. | 604/224 |
| 7,513,889 B2 * | 4/2009 | Jost | 604/207 |
| 7,604,619 B2 | 10/2009 | Eich et al. | |
| 8,361,025 B2 * | 1/2013 | Lawlis et al. | 604/135 |
| 2001/0047153 A1 | 11/2001 | Trocki et al. | |
| 2002/0016571 A1 | 2/2002 | Kirchhofer et al. | |
| 2002/0052578 A1 * | 5/2002 | Moller | 604/208 |
| 2002/0099360 A1 | 7/2002 | Bierman | |
| 2002/0169470 A1 | 11/2002 | Kuhr et al. | |
| 2003/0004466 A1 * | 1/2003 | Bitdinger et al. | 604/218 |
| 2003/0078195 A1 | 4/2003 | Kristensen et al. | |
| 2004/0210199 A1 | 10/2004 | Atterbury | |
| 2004/0215152 A1 * | 10/2004 | Kirchhofer et al. | 604/211 |
| 2004/0236285 A1 * | 11/2004 | Fisher et al. | 604/207 |
| 2004/0238776 A1 | 12/2004 | Peters et al. | |
| 2006/0153693 A1 * | 7/2006 | Fiechter et al. | 417/63 |
| 2007/0123829 A1 * | 5/2007 | Atterbury et al. | 604/207 |
| 2008/0051713 A1 * | 2/2008 | Kohlbrenner et al. | 604/134 |
| 2008/0221530 A1 * | 9/2008 | Glejbol et al. | 604/211 |
| 2008/0234634 A1 * | 9/2008 | Eiland et al. | 604/208 |
| 2008/0243087 A1 * | 10/2008 | Enggaard et al. | 604/208 |
| 2009/0043264 A1 * | 2/2009 | Glejbol et al. | 604/211 |
| 2009/0259197 A1 * | 10/2009 | Christiansen | 604/208 |
| 2009/0275915 A1 * | 11/2009 | Harms et al. | 604/506 |
| 2009/0281505 A1 * | 11/2009 | Hansen et al. | 604/208 |
| 2009/0312717 A1 * | 12/2009 | Christiansen | 604/232 |
| 2010/0010455 A1 * | 1/2010 | Elahi et al. | 604/208 |
| 2010/0016806 A1 * | 1/2010 | Glejbol et al. | 604/211 |
| 2010/0030158 A1 * | 2/2010 | Christiansen | 604/208 |
| 2010/0042054 A1 * | 2/2010 | Elahi et al. | 604/211 |
| 2010/0114025 A1 * | 5/2010 | Moller | 604/135 |
| 2010/0152657 A1 * | 6/2010 | Steenfeldt-Jensen et al. | 604/131 |
| 2011/0046566 A1 * | 2/2011 | Elahi et al. | 604/214 |

FOREIGN PATENT DOCUMENTS

| | | |
|---|---|---|
| DE | 2137405 | 2/1973 |
| DE | 4419235 | 12/1995 |
| DE | 20110690 | 9/2001 |
| EP | 217055 | 4/1987 |
| EP | 549 694 | 7/1993 |
| EP | 762311 | 3/1997 |
| EP | 774270 | 5/1997 |
| EP | 897729 | 2/1999 |
| EP | 8977259 | 2/1999 |
| EP | 897728 | 5/2003 |
| GB | 301961 | 12/1928 |
| GB | 1205201 | 9/1970 |
| GB | 1437595 | 5/1976 |
| GB | 1525455 | 9/1978 |
| GB | 2 214 819 | 9/1989 |
| WO | WO89/02760 | 4/1989 |
| WO | WO 90/09202 | 8/1990 |
| WO | WO92/04926 | 4/1992 |
| WO | WO98/47559 | 10/1998 |
| WO | WO98/56438 | 12/1998 |
| WO | WO00/02605 | 1/2000 |
| WO | WO00/35519 | 6/2000 |
| WO | 0172361 | 10/2001 |
| WO | WO 01/72361 | 10/2001 |
| WO | 02/30490 A2 | 4/2002 |
| WO | WO 02/30490 | 4/2002 |
| WO | WO03/011372 | 2/2003 |
| WO | WO03/011373 | 2/2003 |
| WO | WO 03/017915 | 3/2003 |
| WO | WO2006/069456 | 7/2006 |
| WO | WO 2008/009646 | 1/2008 |

OTHER PUBLICATIONS

English language abstract for CH0501411.
English language abstract for DE2137405.
English language abstract for DE4419235.
Search Report from International Application No. PCT/EP2007/062661, mailed Feb. 25, 2008.
Non-final Office Action in U.S. Appl. No. 12/374,600, sent from the USPTO on Feb. 1, 2010.
Non-final Office Action in U.S. Appl. No. 12/373,339, sent from the USPTO on Jan. 19, 2010.
Novo Nordisk Product Brochure for Insuject-X 1987.
Non-Final Office Action Mailed Apr. 9, 2004 in U.S. Appl. No. 10/230,428, filed Aug. 23, 2002; First Named Inventor: Kristensen.
Non-Final Office Action Mailed Nov. 18, 2004 in U.S. Appl. No. 10/230,428, filed Aug. 23, 2002; First Named Inventor: Kristensen.
Notice of Allowance Mailed May 19, 2005 in U.S. Appl. No. 10/230,428, filed Aug. 23, 2002; First Named Inventor: Kristensen.

(56) References Cited

OTHER PUBLICATIONS

Non-Final Office Action Mailed Feb. 9, 2006 in U.S. Appl. No. 10/230,428, filed Aug. 23, 2002; First Named Inventor: Kristensen.
Notice of Allowance Mailed Oct. 10, 2006 in U.S. Appl. No. 10/230,428, filed Aug. 23, 2002; First Named Inventor: Kristensen.
Non-Final Office Action Mailed Dec. 12, 2006 in U.S. Appl. No. 10/230,428, filed Aug. 23, 2002; First Named Inventor: Kristensen.
Non-Final Office Action Mailed Feb. 10, 2009 in U.S. Appl. No. 11/784,738, filed Apr. 9, 2007; First Named Inventor Kristensen.
Final Office Action Mailed Jun. 2, 2009 in U.S. Appl. No. 11/784,738, filed Apr. 9, 2007; First Named Inventor Kristensen.
Final Office Action Mailed Aug. 12, 2010 in U.S. Appl. No. 12/522,566, filed Sep. 2, 2009; First Named Inventor: Kristensen.
Notice of Allowance Mailed Dec. 13, 2010 in U.S. Appl. No. 12/522,566, filed Sep. 2, 2009; First Named Inventor: Kristensen.
Non-Final Office Action Mailed Oct. 29, 2010 in U.S. Appl. No. 12/305,684, filed Dec. 19, 2008; First Named Inventor: Steenfeldt-Jensen.
Final Action Mailed Jul. 30, 2010 in U.S. Appl. No. 12/373,339, filed Jan. 12, 2009 by Hansen.
Non-Final Office Action Mailed Nov. 24, 2010 in U.S. Appl. No. 12/373,339, filed Jan. 12, 2009 by Hansen.
Non-Final Office Action Mailed Feb. 18, 2011 in U.S. Appl. No. 12/373,340, filed Jan. 12, 2009 by Christiansen.
Non-Final Office Action Mailed Feb. 17, 2011 in U.S. Appl. No. 12/357,013, filed Jan. 21, 2009 by Christiansen.
Final Office Action Mailed Jul. 15, 2010 in U.S. Appl. No. 12/374,600, filed Jan. 21, 2009 by Christiansen.
Non-Final Office Action Mailed Mar. 4, 2011 in U.S. Appl. No. 12/374,600, filed Jan. 21, 2009 by Christiansen.
English Language Abstract of German Patent DE20110690 published Sep. 13, 2001 from Patbase.com.
Eli Lilly HumaPen Ergo Instructions, Copyright 2003, Publication date: Unknown.

\* cited by examiner

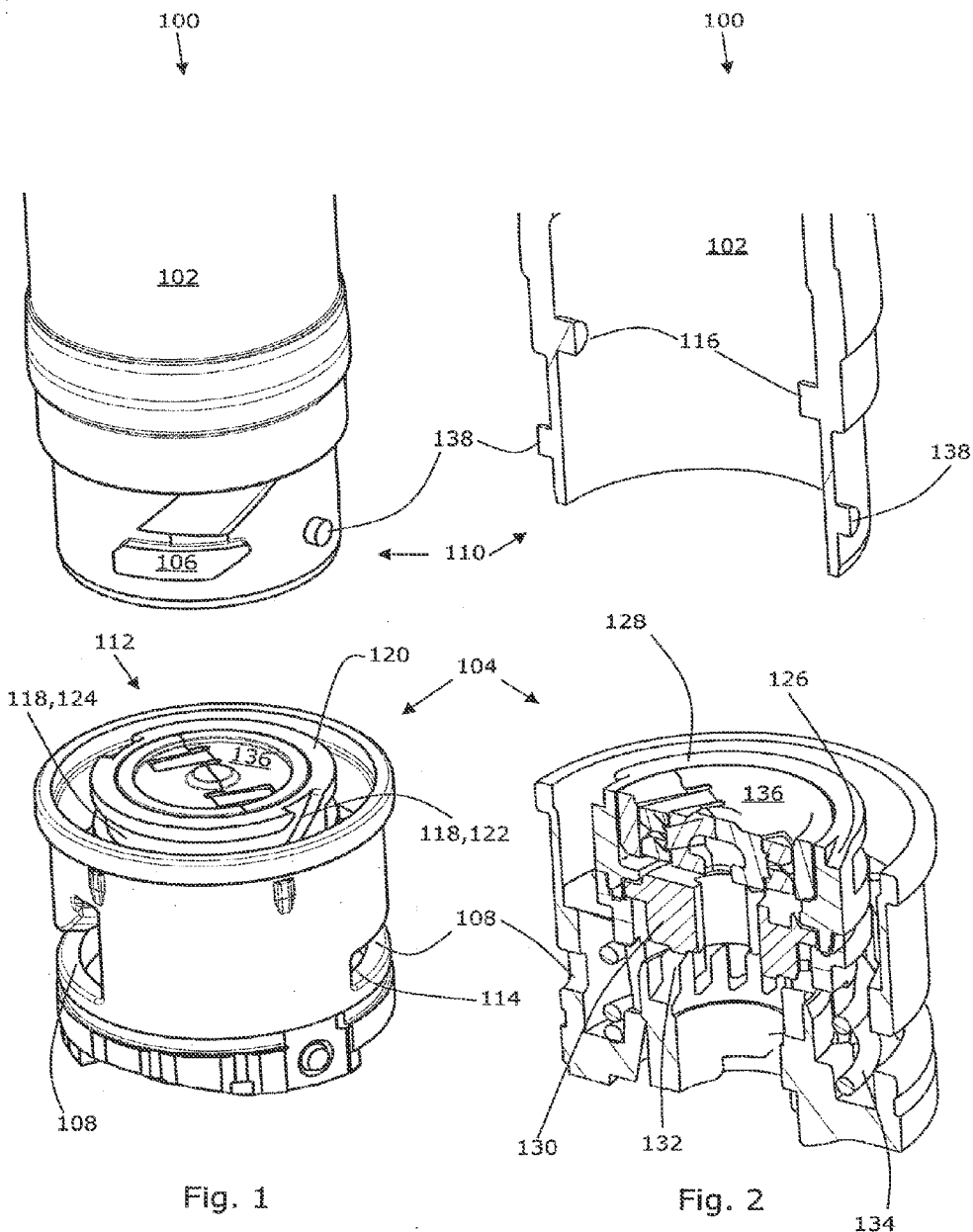

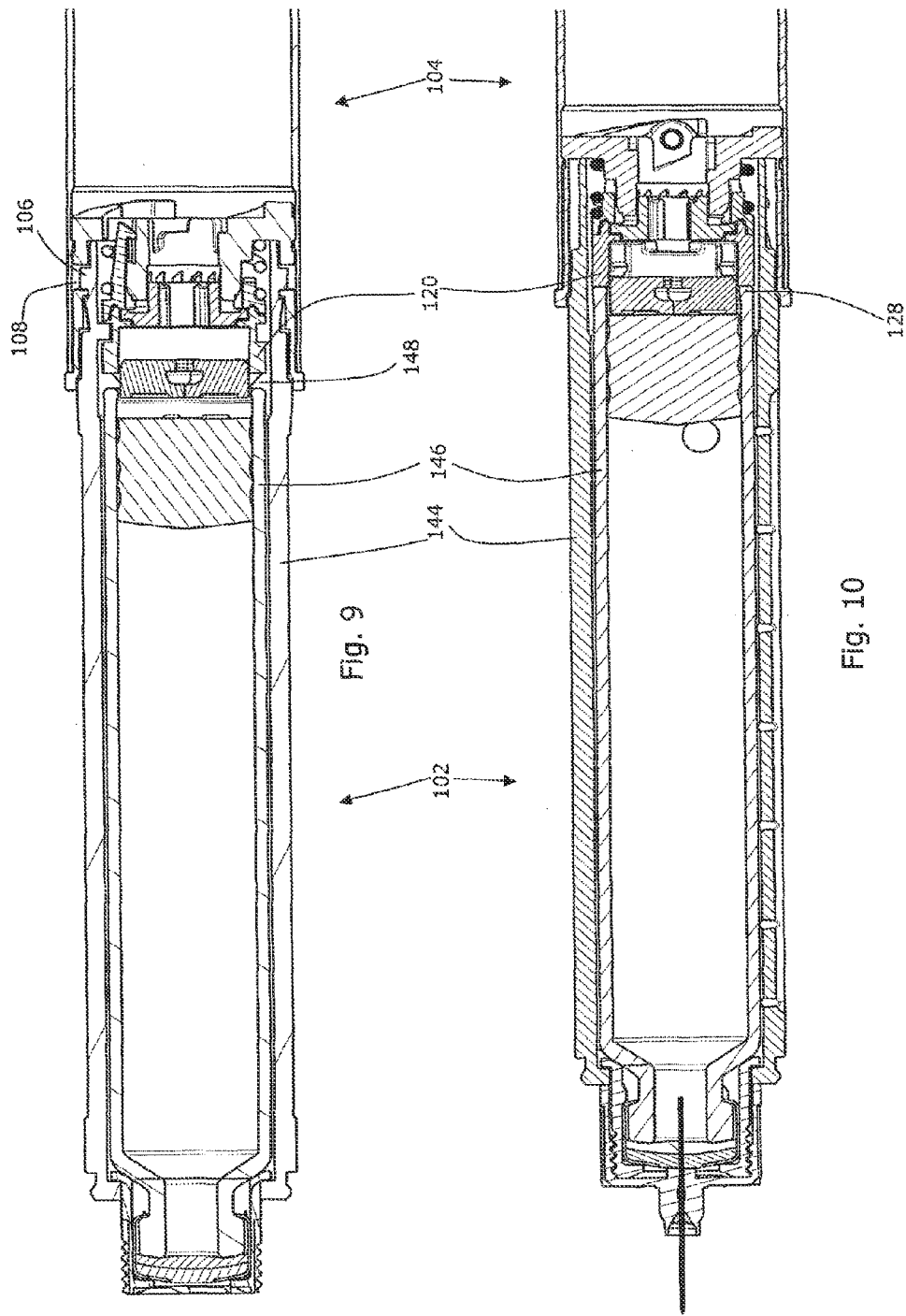

SYRINGE DEVICE

CROSS-REFERENCE TO RELATED APPLICATIONS

This application is a 35 U.S.C. §371 national stage application of International Patent Application PCT/EP2007/064525 (published as WO 2008/074897), filed Dec. 21, 2007, which claimed priority of European Patent Application 06026567.5, filed Dec. 21, 2006; this application further claims priority under 35 U.S.C. §119 of U.S. Provisional Application 60/899,057, filed Feb. 2, 2007.

FIELD OF THE INVENTION

The present invention relates to a medical delivery system comprising a dosing assembly and a container. In particular the present invention relates to a dosing assembly comprising a coupling mechanism movable between a coupling position wherein movement of a drive mechanism in a distal direction is transferred to an actuator and a non-retaining position wherein such movement is not transferred to the actuator. Moreover the present invention relates to a dosing assembly for use in the medical delivery system and a container for use in the medical delivery system. Finally, the present invention relates to medical delivery system comprising a dosing assembly having means for preventing a drive stem of the dosing assembly from being moved in a distal direction.

BACKGROUND OF THE INVENTION

Generally, in order to provide superior medication delivery devices which are likely to be well received by particular groups of patients, a greater diversity in drug delivery systems have been launched to the benefit of patients. As the number of commercially available delivery systems increase, numerous different types of medication holding cartridges or containers are distributed. Most of these types of containers differ in various aspects.

Each medicament container may be filled with a particular type of medicament selected from a large variety of different medicaments, but also different kinds of the same class of medicament (e.g. rapid or long acting insulin) and different concentrations of each particular medicament may be accommodated in the containers.

Moreover, different container volumes may be introduced in order to customize each container, and thus the delivery system, to the needs of particular users. Variation of container volume may be provided by changing the length or diameter of the container. These modifications usually imply corresponding modifications of the dosing assembly of a medication delivery system, so as to provide a particular stroke of a driving element for expelling the medicament from the container or to provide optimal dosing precision. Further discrimination between different medicament containers may be occasioned by the design requirements for each particular delivery system, such as required sliding friction of the piston accommodated in the container.

In order to discriminate between a larger variety of available containers, numerous container coding and coupling systems have been developed. The following mechanical coding and coupling systems are known in the art:

U.S. Pat. No. 5,611,783 relates to a pen shaped syringe comprising a distal part which may comprise an ampoule and a proximal part containing a dose setting and drive mechanism. The proximal and distal parts have interlocking bayonet coupling means. Protrusions may be provided to form a pattern ensuring that a certain distal part may only be used in connection with a certain proximal part.

WO 03/017915 A1 discloses a cartridge having a distal end provided with a mechanical coding. The mechanical coding has the form of a circular protrusion where the circular outer diameter is dedicated a specific concentration of insulin contained in the cartridge.

U.S. Pat. No. 5,693,027 discloses a plastic top for adapting a standard cartridge to a chosen syringe. The plastic top may be provided with means for keyed engagement with corresponding means in a syringe to keep it unrotatable when mounted with a cartridge in the syringe. In some types of syringes such keyed engagement between cartridge and syringe is further used to ensure that only a certain type of cartridge is used.

U.S. Pat. No. 6,648,859 B2 discloses a drug cartridge assembly for use with a reusable pen body assembly of a medication delivery pen. In order to eliminate cross-use the pen body assembly and the drug cartridge are keyed i.e. they may be threadedly engaged by corresponding threads and grooves, bayonet threads, and grooves, snap fits or a pair of lugs that mate in reverse Luer-Lock manner. The mating members are selected so as to prevent cross-use with other assemblies, e.g., the pitch of the threads may be angled so as to mate only with one another and not with other assemblies.

Yet another prior art system is described in DE 201 10 690.

U.S. Pat. No. 5,584,815 discloses a lock and pullback mechanism which prevents rotation of a lead screw upon metering and injection. The pullback sleeve unloads a pullback key during cartridge change in order to enable the leadscrew to be spun freely back to its home position.

It is an object of a preferred embodiment of the present invention to provide an alternative to the known systems. Furthermore, it is an object of a preferred embodiment of the present invention to provide a medication delivery system with a large number of possible coding geometries.

Furthermore, it is an object of a preferred embodiment of the present invention to provide a coding system wherein the user experiences substantially the same operational fastening/coupling/locking movement when the container and dosing assembly of a predetermined medical delivery system are coupled/uncoupled (locked/unlocked) to each other regardless of the specific choice among sets of compatible container/dosing assemblies.

Furthermore, it is an object of a preferred embodiment of the present invention to provide an intuitive and simple fastening mechanism for fastening the container to the dosing assembly.

Furthermore, it is an object of the present invention to provide a medical delivery system wherein the influence of the tolerances of a glass cartridge may be reduced or even eliminated.

Furthermore, it is an object of the present invention to provide a medical delivery system having an alternative mechanism for allowing resetting of an actuator during a container change.

BRIEF DESCRIPTION OF THE INVENTION

In a FIRST aspect the present invention relates to a medical delivery system comprising:
 a container adapted to contain a medicament in a chamber defined by the container and a slidably arranged piston which is movable in a distal direction towards an outlet so as to reduce the volume of the chamber and expel the medicament through the outlet;

a dosing assembly adapted to be fastened to the container and comprising:
- an actuator for advancing the piston in the distal direction,
- a drive mechanism for advancing the actuator in the distal direction, and
- a coupling mechanism movable between a distal position wherein movement of the drive mechanism in the distal direction is not transferred to the actuator, and a proximal position wherein movement of the drive mechanism in the distal direction is transferred to the actuator whereby the piston is moved in the distal direction and the medicament is expelled; and wherein one of the container and the dosing assembly defines one or more radially extending fastening projections each of which during fastening of the container to the dosing assembly engages a corresponding radially extending fastening groove of the other one of the dosing assembly and the container whereby the container is fastened to the dosing assembly; and wherein one of the container and the coupling mechanism defines one or more radially extending retaining projections each of which during fastening of the container to the dosing assembly engages a corresponding radially extending retaining groove of the other one of the coupling mechanism and the container, whereby the coupling mechanism is moved from the distal position to the proximal position.

Compared to medical delivery systems wherein a glass cartridge of the container is adapted to move the coupling mechanism from the distal to the proximal position, the present invention provides the advantage that the chain of tolerances is reduced. In conventional systems the chain of tolerances between the dosing assembly and the coupling mechanism is dependent on the tolerances of the cartridge holder and a glass cartridge. As a predetermined level of tolerances are cheaper to achieve by use of plastic moulding than by glass moulding, the present invention provides a cheap alternative to known systems.

In the context of the present invention the term "medical delivery system" shall be understood as any system capable of administering a medicament-containing flowable drug. Examples of medical delivery systems are infusion pump applications, dosers, pen-shaped dosers, motor-dosers, and automated syringes such as the AutoPen™.

The invention is applicable to all kinds of medicament delivery devices capable of delivering a medicament to a user from a container which is adapted to be coupled to a dosing assembly of the delivery device. The delivery device may include any delivery device for transcutaneous, subcutaneous, intravenous, intra muscular or pulmonary administration of a drug.

As used herein, the term "medicament" is meant to encompass any medicament-containing flowable drug capable of being passed through a delivery means such as a hollow needle in a controlled manner, such as a liquid, solution, gel or fine suspension. Representative medicaments includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The chamber of the container may be defined by one or more sidewalls of the container and the slidably arranged piston. In most embodiments at least a part of the container is ringshaped (i.e. having a cylindrical cross-section) and defines a cylindrical cavity in which the piston is received.

The distal end of the container may comprise a seal for penetration by a cannula so as to allow a medicament contained in the chamber to be expelled through the cannula. The distal end of the container may be adapted to be attached to a holder holding a cannula. As an example the distal end of the container may comprise a thread adapted to cooperate with a corresponding thread of the cannula holder so as to allow the cannula holder to be screwed onto the container.

In one embodiment the container comprises a cartridge holder and a cartridge defining said chamber. The cartridge and the cartridge holder may be two separate elements, and the cartridge may be frictionally retained in the cartridge holder. In one embodiment the cartridge is made of glass and the cartridge holder is made of a non-glass material for protecting the glass cartridge. The cartridge may be non-removably retained in the cartridge holder, such that if the cartridge is removed from the cartridge holder it cannot be reattached by hand and without tools. This provides the advantage that the cartridge holder cannot be reused when the cartridge has been emptied, accordingly a cartridge with a wrong medicament cannot be inserted into the cartridge holder and be dispensed by use of the dosing assembly. The cartridge holder and the cartridge may define a monolithic element, i.e. forming one element without seams. Such a monolithic element may be formed as a moulded article made of a synthetic resin such as Topas® or polypropylene. Such a moulded article may include the fastening and coding geometries which are formed during moulding. However, any material which is suitable for long-term storage of the specific medication to be accommodated in the container may be used.

The outlet of the container may be adapted to cooperate with or be defined by a cannula or a needle or a needle hub or an infusion set, or any other fluid communicating conduit adapted to provide fluid access to a medicament accommodated in the container.

In the context of the present invention the terms "depression" and "projection" are only used in connection with radially extending members/elements/means, and "indentation" and "protrusion" are only used in connection with axially extending members/elements/means. However, "depression" and "indentation" shall be seen as synonyms and "protrusion" and "projection" shall be seen as synonyms. The actuator may be adapted to abut/engage the piston such that movement of the actuator in the distal direction causes the piston to be moved in the distal direction. In most embodiments movement of the actuator in the proximal direction causes the actuator to disengage the piston, while the piston remains in same axial position, whereby movement of the actuator in the proximal direction does not cause air to be sucked into the chamber of the container.

The drive mechanism may comprise a dosing knob accessible from an outer surface of the medical delivery system in order to allow a user to set a dose. The dosing knob may define a proximal end of the dosing assembly. In one embodiment the user sets a dose by rotating the dosing knob about the main axis of the medical delivery system, whereby the dosing knob is moved in the proximal direction. When the dose is set, it may be ejected by forcing the dosing knob in the distal direction, whereby the medicament is ejected.

One of the container and the dosing assembly defines one or more radially extending fastening projections each of which during fastening of the container to the dosing assembly engages a corresponding radially extending fastening groove of the other one of the dosing assembly and the container whereby the container is fastened to the dosing assembly. In one embodiment the container defines a plurality of radially extending fastening projections such as one, two, three, four or five, and the dosing assembly defines a corresponding number of radially extending fastening grooves. In another embodiment the dosing assembly defines a plurality of fastening projections and the container defines a corresponding number of fastening grooves.

The particular set of fastening projections and fastening grooves may be so configured that the fastening procedure of the container to the dosing assembly includes an initial relative axial movement followed by a relative rotational locking movement. In some embodiments, the fastening procedure includes an intermediary movement between the initial axial movement and the rotational locking movement, where the intermediary movement includes a concurrent relative rotational and axial movement.

Moreover, one of the container and the coupling mechanism defines one or more radially extending retaining projections each of which during fastening of the container to the dosing assembly engages a corresponding radially extending retaining groove of the other one of the coupling mechanism and the container, whereby the coupling mechanism is moved from the proximal position to the distal position.

In one embodiment the container defines a plurality of retaining projections such as two, three, four or five, on its inner surface, and the coupling mechanism defines a corresponding number of retaining grooves on its outer circumferential surface. In another embodiment the retaining projections are defined on the outer surface of the coupling mechanism and the retaining grooves are defined on an inner surface of the container.

In one embodiment the retaining groove is defined in an outer surface of the coupling mechanism such that the groove extends radially into the coupling mechanism from an outer surface thereof (and towards the centre axis of the coupling mechanism). Moreover in said embodiment, the retaining projection is defined on an inner surface of the container, i.e. such that it extends away from said surface and towards a centre axis of the container.

In another embodiment the retaining groove is defined in an inner surface of the container such that the groove extends radially into the container from its inner surface, i.e. away from the centre axis of the container. In said other embodiment, the retaining projection extends radially outwards from the outer surface of the coupling mechanism, i.e. away from the centre axis of the coupling mechanism.

In one embodiment at least a part of the dosing assembly encircles at least a part of the container when the container is fastened to the dosing assembly, e.g. a distal end/part of the dosing assembly may encircle a proximal end/part of the container. Moreover, at least a part of the container may encircle at least a part of the coupling mechanism, when the container is fastened to the dosing assembly. As an example a proximal part/end of the container may encircle a distal part of the coupling mechanism. At least a part of the coupling mechanism may be received in the dosing assembly, e.g. such that most of or the entire coupling mechanism is encircled by the dosing assembly. It will be appreciated, that the above-mentioned radial order of elements may be reversed e.g. such that the container encircles the dosing assembly when said two elements are fastened to each other.

In one embodiment the container is inserted between the coupling mechanism and the dosing assembly during fastening, such that an outer part of the container is coupled to the dosing assembly and such that an inner part of the container is coupled to the coupling mechanism. Said outer part may be the fastening projection. Said inner part may be the retaining projection.

Each of the one or more retaining grooves may define a first groove part which, during fastening of the container to the dosing assembly, is adapted to guide the corresponding retaining projection into a second groove part of the retaining groove. The second groove part may be shaped so as to allow relative rotational movement between the container and the coupling mechanism.

The general direction of the first groove part and the general direction of the second groove part may define an angle different from 180 degrees. In the present context the term "general direction" shall be understood as the direction of a line positioned in the groove such that the distance at any point along the line to each of two opposing sidewalls of the groove is identical. In one embodiment the general direction of the first groove part defines an angle of between 20 and 80 degrees (such as between 30 and 60 degrees) relative to the general direction of the second groove part.

In order to allow the retaining projection to be received in the retaining groove, the first groove part may define an inlet of the retaining groove. At least a part of the inlet may be defined on a distal facing surface of the coupling mechanism. In one embodiment the retaining groove is defined in an outer circumferential surface of the coupling mechanism such that the groove extends into the coupling mechanism from a surface thereof. In the latter embodiment the first groove part commences at the distal end of the dosing assembly such that an inlet is defined in the distal end surface of the coupling mechanism. Accordingly, by advancing the container in a proximal direction (towards the dosing assembly) a corresponding retaining projection of the container is received in the first groove part by being moved into said groove part through the inlet. Upon further axial and/or rotational movement, the retaining projection is moved from the first groove part and into the second groove part.

The second groove part may be shaped such that, when the retaining projection is positioned in the second groove part, translational/axial movement of the container in the proximal direction causes the coupling mechanism to be moved towards the proximal position. The second groove part may define a proximal and/or a distal facing sidewall. Upon proximal movement of the container relative to the dosing assembly a proximal facing surface of the retaining projection may abut the distal facing sidewall of the second groove part, whereby said proximal movement of the container is transferred to the coupling mechanism. Accordingly, the coupling mechanism may be moved from the distal position into the proximal position during fastening of the container to the dosing assembly.

The second groove part may extend circumferentially on an inner or outer surface of the container or coupling mechanism, respectively. In one embodiment the second groove part defines a circular groove extending on the outer surface of the coupling mechanism or on the inner surface of the container. The circular groove may define a geometrical centre coinciding with the centre axis of the coupling mechanism or the container. In another embodiment, the second groove part defines an arc shaped groove, i.e. defining a segment of a circle, having a geometrical centre point coinciding with the centre axis of the container or the coupling mechanism. The angular extent of the segment (about its geometrical centre point) may be less than 180 degrees, such as less than 120 degrees, such as less than 90 degrees, such as less than 45 degrees, such as less than 30 degrees.

The fastening groove, the fastening projection, the retaining groove and the retaining projection may be arranged with respect to each other, such that upon movement of the fastening projection into the inlet of the fastening groove, the retaining projection is received in the inlet of the retaining groove. In one embodiment the fastening groove, the fastening projection, the retaining projection and the retaining groove are arranged with respect to each other such that the fastening projection is received in the fastening groove prior to the retaining projection is received in the retaining groove. In a further embodiment the order is reversed such that the retaining projection is received in the retaining groove prior to the fastening projection is received in the fastening groove.

The actuator may comprise a piston rod which is connected to a drive stem adapted to abut the piston. The drive stem may have larger diameter than the piston rod such as a diameter above 75% of the diameter of the piston and/or a diameter at least three times larger than the piston rod.

In one embodiment the piston rod has a threaded outer surface which is adapted to engage a corresponding surface of the dosing assembly and/or the coupling mechanism. Upon rotation between the piston rod and the dosing assembly and/or the coupling mechanism, the piston rod is moved axially. In a further embodiment, the piston rod is locked for rotation relative to the dosing assembly and/or the coupling mechanism when the coupling mechanism is positioned in the proximal position, whereby a piston rod with a threaded outer surface, is retained axially. Moreover in said embodiment, the piston rod is allowed to rotate relative to the dosing assembly and/or the coupling mechanism, when the coupling mechanism is positioned in the distal position, thus allowing the piston rod to be moved axially in the distal and/or proximal direction. Accordingly in the latter embodiment, the piston rod is locked for movement in the proximal direction when the container is fastened to the dosing assembly, while the piston rod may be moved/rotated into its initial/proximal position when the container has been removed e.g. during replacement of a container so as to reset the piston rod.

In each of the above embodiments, the coupling mechanism comprises a rotatable guide member disposed circumferentially with respect to the piston rod. When the coupling mechanism is positioned in the proximal position, the rotatable guide member is rotationally locked with respect to a housing section of the dosing assembly whereas when the coupling mechanism is positioned in the distal position, the rotatable guide member is free to rotate with respect to the housing.

The piston rod and the rotatable guide member may form a keyed engagement allowing relative axial movements between the piston rod and the rotatable guide member but constraining relative rotational movements. In embodiments where the drive mechanism of the dosing assembly is configured to move the piston rod purely axially when expelling a medicament, the piston rod may be formed with one or more axially extending tracks each of which is adapted to receive a radially inwards extending protrusion formed in the rotatable guide member. In embodiments where the drive mechanism is configured to move the piston rod rotationally during expelling of a medicament, the piston rod is formed with one or more threaded portions engaging corresponding one or more threaded segments of the rotatable guide member.

Fastening of a wrong container to the dosing assembly may have serious consequences as a wrong dose of a medicament or a wrong medicament may be ejected. Accordingly, it is desirable that a medicament of a container wrongly connected to the dosing assembly of the present invention is prevented from being expelled. This may be achieved by preventing the drive stem from being advanced in the distal direction when a wrong container is fastened to the dosing assembly.

In one embodiment the effect is achieved by providing a dosing assembly which defines one or more axially extending protrusion(s) each of which is movable/bendable between a retaining position wherein each of the protrusions retains the drive stem in an initial position and a non-retaining position in which the drive stem, when positioned in the initial position, is allowed to be moved in the distal direction. Accordingly, only medicaments of containers shaped so as to allow the axially extending projection(s) to be positioned in the non-retaining position can be expelled by means of the dosing assembly. As an example, the one or more axially extending protrusions may be defined by/on the coupling mechanism. Each of protrusions may be adapted to bend about a bending axis which is parallel with a tangent of the coupling mechanism and/or the dosing assembly.

In one embodiment the container is shaped such that when fastened to the dosing assembly, each of the axially extending protrusions is allowed to move between the retaining and non-retaining position, whereby the drive stem, when positioned in the initial position, may be advanced in the distal direction. In a further embodiment the axially extending protrusion extend from a distal facing surface of the coupling mechanism and is bendable between the retaining and the non-retaining position such that when bended towards the centre of the coupling mechanism the protrusions are moved into the retaining position. Moreover, the distal end of each of the protrusions may define an inclined surface such that a container abutting the inclined surface forces the protrusions towards the retaining position.

Accordingly, in one embodiment the container is shaped such that when fastened to the dosing assembly, the container does not abut the inclined surface(s) and thus the axially extending protrusions are not forced towards/into the retaining position.

In one embodiment the distal end of the coupling mechanism may define first areas in which the axially extending projections are defined and second areas in which no axially extending projections are defined. Moreover in the latter embodiment, the container may be adapted to abut the coupling mechanism in one or more of the second areas when the container is fastened to the dosing assembly, while at the same time the container does not abut any of the axially extending projections.

In one embodiment the one of the container and the dosing assembly comprises one or more radially coding projection(s) each of which during fastening of the container to the dosing assembly is adapted to be received in a corresponding radially extending coding groove defined in the other one the container and the dosing assembly. In one embodiment, the coding projections and the fastening projections are identical, i.e. each fastening projection defines a coding projection. In another embodiment, the coding projections and the fastening projections are defined by different projections of the container or the dosing assembly. Additionally, the fastening grooves and the coding grooves may be identical or define separate grooves of the container or the dosing assembly.

The coding projection(s) and/or the coding groove(s) may define predetermined coding geometries preventing the container from being fastened to the dosing assembly unless each of the coding projections and/or coding grooves defines a predetermined coding geometry which is selected from a predetermined group of coding geometries. The coding geometry of each of the coding projections and/or the coding grooves may be defined by at least one of:

a circumferential extent of the coding projection and/or the coding groove, an axial extent of the coding projection and/or the coding groove, a radial extent of the coding projection and/or the coding groove and a circumferential position of the coding projection and/or the coding groove.

Moreover, the retaining projection(s) and/or the retaining groove(s) may define predetermined coding geometries preventing the container from being fastened to the dosing assembly unless each of the retaining projections and/or retaining grooves defines a predetermined coding geometry which is selected from a predetermined group of coding geometries. The coding geometry of each of the retaining projections and/or the retaining grooves may be defined by at least one of:

a circumferential extent of the retaining projection and/or the retaining groove, an axial extent of the retaining projection and/or the retaining groove, a radial extent of the retaining projection and/or the retaining groove and a circumferential position of the retaining projection and/or the retaining groove.

In one embodiment the medical delivery system comprises:

a first container according to the first aspect of the invention adapted to be fastened to a first dosing assembly according to the first aspect of the invention; and a second container according the first aspect of the invention adapted to be fastened to a second dosing assembly according to the first aspect of the invention; and wherein at least one of the retaining groove, the retaining projection, the fastening groove and the fastening projection is/are adapted to prevent the first dosing assembly and second container from being fastened to each other, and to prevent the second dosing assembly and the first container from being fastened to each other.

The medical delivery system according to first aspect of the invention may comprise any combination of features and elements of the invention according to the second and/or third, and/or fourth aspect of the invention.

In a SECOND aspect the present invention relates to a container for use in the medical delivery system according to the first aspect of the invention, the container comprising at least one fastening projection extending in a radial direction from an outer surface the container, and at least one retaining projection extending in a radial direction from an inner surface of the container.

The container according to the second aspect of the invention may comprise any combination of features and elements of the invention according to the first or fourth aspect of the invention. As an example the container may comprise a coding projection extending in a radial direction from the outer surface of the container. The position of any of the fastening projections and the position of any of the coding projections are arranged so that they do not coincide.

In one embodiment the fastening projection(s) are proximal relative to the retaining projection(s) or vice versa. Alternatively, the axial position of at least one fastening projection and the axial position of at least one retaining projection are substantially identical.

In a THIRD aspect the present invention relates to a dosing assembly for use in the medical delivery system according to the first aspect of the invention, comprising an actuator movable in a distal direction, a drive mechanism for advancing the actuator on the distal direction and a coupling mechanism (axially) movable between a distal position wherein movement of the drive mechanism in the distal direction is not transferred to the actuator, and a proximal position wherein movement of the drive mechanism in the distal direction is transferred to the actuator, and wherein a retaining groove is defined on an outer circumferential surface of the coupling mechanism, and a fastening groove is defined on an inner surface of the dosing assembly.

The invention according to the third aspect may comprise any combination of features and elements of the invention according to the first or fourth aspect of the invention. As an example the retaining groove may define a first and a second groove part. The second groove part may extend circumferentially on the outer surface of the coupling mechanism and may cover an angular segment of at least 45 degrees of the circumference of the coupling mechanism.

In a FOURTH aspect the present invention relates to a medical delivery system comprising:

a container adapted to contain a medicament in a chamber defined by the container and a slidably arranged piston which is movable in a distal direction towards an outlet so as to reduce the volume of the chamber and expel the medicament through the outlet;

a drive stem for advancing the piston in the distal direction;

a dosing assembly adapted to be fastened to the container and to accommodate the drive stem when said drive stem is positioned in an initial position;

wherein the dosing assembly defines one or more axially extending protrusion(s) each of which is movable between a retaining position wherein each of the protrusions prevents the drive stem, when positioned in the initial position, from being moved in the distal direction, and a non-retaining position wherein the drive stem, when positioned in the initial position, is allowed to be moved in the distal direction; and wherein the container is shaped such that when fastened to the dosing assembly, each of the axially extending protrusions is free to move between the retaining and non-retaining position whereby the drive stem, when positioned in the initial position, may be advanced in the distal direction.

The invention according to the fourth aspect of the invention may comprise any combination of features or elements of the invention according to the first aspect of the invention.

In a FIFTH aspect the present invention relates to a medical delivery system comprising:

a container adapted to contain a medicament in a chamber defined by the container and a slidably arranged piston which is movable in a distal direction towards an outlet so as to reduce the volume of the chamber and expel the medicament through the outlet;

a dosing assembly adapted to be fastened to the container and comprising:

an actuator for advancing the piston in the distal direction, a drive mechanism for advancing the actuator in the distal direction, and a coupling mechanism including a rotatable guide member which engages the actuator, the rotatable guide member being either rotationally locked with respect to the actuator or being threadedly engaged with the actuator, the coupling mechanism being movable between a distal position wherein the rotatable guide member is free to rotate in the dosing assembly and wherein movement of the drive mechanism in the distal direction is not transferred to a distal movement of the actuator and a proximal position wherein the rotatable guide member is rotationally locked in the dosing assembly and wherein movement of the drive mechanism in the distal direction is transferred to the actuator whereby the piston is moved in the distal direction and the medicament is expelled; and wherein one of the container and the dosing assembly defines one or more radially extending fastening projections each of which during fastening of the container to the dosing assembly engages a corresponding radially extending fastening groove of the other one of the dosing assembly and the container whereby the container is fastened to the dosing assembly, the fastening projections and grooves being adapted to fasten the container to the dosing assembly by a relative translational movement along an axis followed by a relative rotational locking movement around the axis; and wherein one of the container and the coupling mechanism comprises an inclined surface portion adapted, responsive to said relative locking movement, to engage an engagement surface of the other of the container and the coupling mechanism, the inclined surface portion being arranged to move the coupling mechanism from the distal position to the proximal position upon said relative locking movement.

Compared to medical delivery systems of the type having a rotatable guide member in engagement with the actuator/piston rod, where the rotatable guide member is adapted to become rotationally locked relative to a housing part of the dosing assembly upon axially coupling the container to the dosing assembly, the invention according to the fifth aspect provides for an improved resetting of the actuator/piston rod upon container/cartridge change where pressure build-up in the container. According to the fifth aspect of the invention, the coupling mechanism ensures that rotational locking of the rotatable guide member is postponed until the moment where a user locks the container to the dosing assembly by the relative rotational locking movement, i.e. after the container has been substantially or fully axially engaged with the dosing assembly.

The container and/or the dosing assembly may in some embodiments comprise more than one inclined surface, such as two, three or more, each adapted to engage respective engagement surfaces of the other of the container and the dosing assembly.

In some embodiments, one or more of the inclined surfaces are arranged on the container part. The inclined surfaces may be formed as ramp shaped protrusions arranged on a proximal rim portion of the container. Alternatively, the or each of the inclined surfaces may be formed as an inclined groove formed in an inner wall section of the container. Still, alternatively, the inclined surface feature may be provided as a radially inwards projection forming an inclined track along an inner surface of the container arranged to move the coupling mechanism of the dosing assembly into its proximal position upon relative rotation between the container and the dosing assembly.

The invention according to the fifth aspect of the invention may comprise any combination of features or elements of the invention according to the first and fourth aspect of the invention provided that they form a compatible combination with the fifth aspect.

BRIEF DESCRIPTION OF THE DRAWINGS

In the following the invention will be described with reference to the drawings in which:

FIG. 1 discloses an isometric view of an embodiment of the invention according to the first aspect, FIG. 2 discloses a sectional view of FIG. 1, FIG. 3 discloses an isometric view of the coupling mechanism, FIG. 4 discloses an isometric view of a part of the dosing assembly, FIG. 5 discloses an isometric and exploded view of two parts of the dosing assembly, FIGS. 6-8 disclose the process of fastening the container to the dosing assembly, FIGS. 9-10 disclose two medical delivery systems, FIGS. 11-13 disclose an embodiment of the invention according to the first and fourth aspect of the invention, and FIGS. 14-16 disclose an embodiment of the invention according to the fifth aspect of the invention.

DETAILED DESCRIPTION OF THE DRAWINGS

Figure 3:
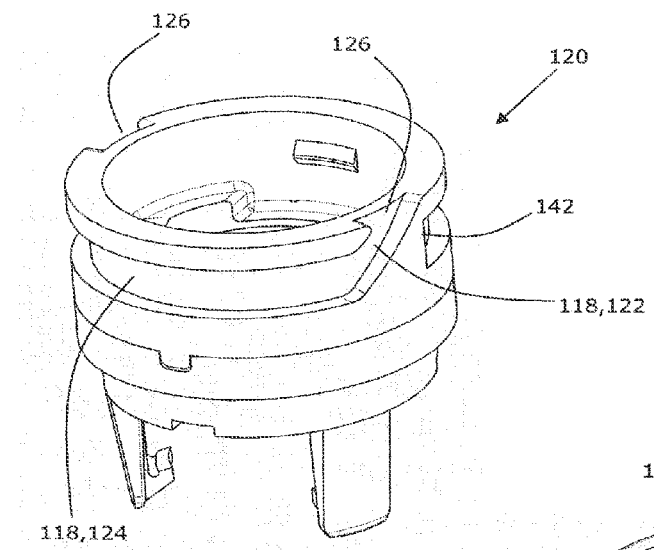

FIGS. 1 and 2 disclose a medical delivery system 100 comprising a container 102 and a dosing assembly 104. The container 102 is adapted to be fastened to the dosing assembly 104 by engagement between a fastening projection 106 of the container 102 and a corresponding fastening groove 108 of the dosing assembly 104. Container 102 forms a distally arranged expelling portion adapted to engage patient access means such as an injection needle.

Dosing assembly 104 includes an actuator/piston rod (not shown) being driveable by a suitable drive mechanism (not shown) to force a piston arranged in container 102 towards a distal end of the medical delivery system 100. As non-limiting examples of suitable drive mechanisms, reference is made to WO 01/95959 and WO 2006/114395.

During fastening, a proximal end 110 the container 102 is moved axially into a distal end 112 of the dosing assembly 104 such that the fastening projection 106 is received in the fastening groove 108. In order to fasten the container 102 to the dosing assembly 104, the container 102 is rotated clockwise relative to the dosing assembly 104, whereby the fastening projection 106 is moved into an end part 114 of the fastening groove 108. Accordingly, the container 102 is fastened to the dosing assembly 104 by an initial axial movement followed by a combined axial and rotational movement.

The dosing assembly 104 comprises a coupling mechanism 120 which is adapted to restrain rotational movement of an actuator/piston rod with respect to a housing part of the dosing assembly, when the container 102 is properly connected to the dosing assembly 104.

During fastening, a retaining projection 116 of the container 102 engages a retaining groove 118 of a coupling mechanism 120 of the dosing assembly 104. The retaining groove 118 comprises a first part 122 and a second part 124. The first part defines an inlet 126 on a distal surface 128 of the coupling mechanism 120. During fastening the retaining projection 116 is advanced into the first part 122 through the inlet 126. Upon further axial and rotational movement the retaining projection 116 is moved from the first part 122 into the second part 124. When the retaining projection 116 is positioned in the second part 124 axial movement of the container 102 relative to the dosing assembly 104 causes the coupling mechanism 120 to be moved from a distal position (shown in FIGS. 1, 2 and 7) and into a proximal position (shown in FIG. 9).

The coupling mechanism 120 includes a rotatable guide member 130 which encircles the actuator/piston rod. On an internal radially inwards facing surface of the rotatable guide member 130, the rotatable guide member includes a plurality of protrusions forming a keyed engagement with tracks formed in the actuator/piston rod. The tracks of the actuator/piston rod is provided as axially extending tracks whereby the actuator/piston rod is rotationally fixed but axially translatable with respect to the rotatable guide member 130. Alternatively, the actuator/piston rod forms one or more helical tracks into which the protrusions of the rotatable guide member 130 are adapted to be received. In such an embodiment, during expelling of medicament from a container, the actuator/piston rod is adapted to be rotationally guided, i.e. the rotation of the actuator/piston rod is a function of the axial displacement.

When the coupling mechanism 120 is positioned in the distal position, the rotatable guide member 130 is free to rotate whereby movement of the drive mechanism (not shown) in the distal direction is not transferred to the actuator/piston rod. When the rotatable guide member is free to rotate, the actuator/piston rod may be rotated back to a proximal home position. Moreover, when the coupling mechanism 120 is positioned in the proximal position, the rotatable guide member 130 is rotationally locked with respect to housing of the dosing assembly 104 and movement of the drive mechanism in the distal direction is transferred to the actuator/piston rod whereby the piston is moved in the distal direction and the medicament is expelled.

When the coupling mechanism 120 is positioned in the distal direction, rotatable guide member 130 is free to rotate relative to the housing of the dosing assembly 104, as teeth 131 of rotatable guide member 130 (receiving the piston rod) do not engage corresponding teeth 132 of the dosing assembly 104. Hence, the actuator/piston rod (not shown) is allowed to be rotated relative to the dosing assembly 104. When the coupling mechanism 120 is positioned in the proximal position the aforementioned teeth engage and lock the rotatable guide member 130 against rotation. In the latter position the actuator/piston rod is rotatively guided as determined by the axial track of the actuator/piston rod and movement of a drive mechanism in the distal direction causes the actuator/piston rod to be moved in the distal direction.

The coupling mechanism 120 is biased towards the distal position due to the spring 134, accordingly when a container 102 is not fastened to the dosing assembly 104, the coupling mechanism 120 is positioned in the distal position and the actuator/piston rod is free to be moved in the proximal (and distal) direction by the user. Thus, when a container 102 has been emptied the user may "rewind" the actuator/piston rod by removing the container and resetting the actuator/piston rod by forcing it in the distal direction by finger pressure. Alternatively, resetting of the actuator/piston rod occurs by allowing the new container to push the actuator/piston rod to its home position when axially engaging the new container with the dosing assembly.

The actuator comprises a piston rod (not shown) received in a drive stem 136. The drive stem 136 and the piston rod are locked axially to each other but allowed to be rotated relative to each other about a centre axis of the piston rod.

Figure 4:
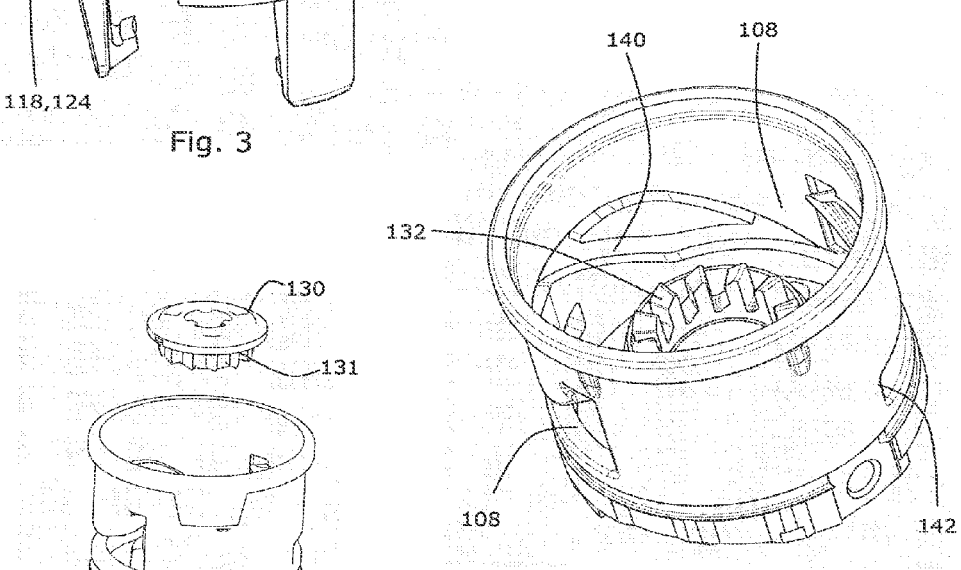

In order to ensure that only predetermined containers 102 are fastened to predetermined dosing assemblies 104, the container 102 defines at least one coding projection 138 each of which are adapted to be received in a corresponding coding groove 140 of the dosing assembly 104 as shown in FIG. 4.

FIG. 3 discloses a part of the coupling mechanism 120 which defines the retaining groove 118. As described above, the retaining groove 118 defines a first part 122 and a second part 124. The first part 122 defines an inlet 126 of the retaining groove 118. The first part 122 is adapted to guide the retaining projection 116 from the inlet 126 into to the second part 124. When the retaining projection 116 has entered the second part 124 clockwise rotation of the container 102 relative to the coupling mechanism 120 moves the retaining projection 116 towards a bottom surface 142 of the second part 124. When the retaining projection 116 abut the bottom surface 142, the container 102 is locked for clockwise rotation relative to the dosing assembly 104.

Figure 5:
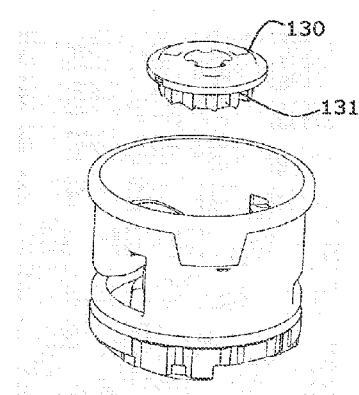

The coding groove 140 is visible in the embodiment of FIG. 4. In the latter embodiment movement of the coding projection 138 in the coding groove 140 causes the coding projection 138 to be moved into a part of the fastening groove 108. However, in other embodiments the coding groove 140 and the fastening groove 108 are not connected. As described in the aforementioned, the dosing assembly 104 comprises teeth 132 which are engaged by teeth 131 of the coupling mechanism 120, when the latter is moved from the distal position to the proximal position. The teeth 131 of the coupling mechanism 120 are visible in FIG. 5.

Figure 6:
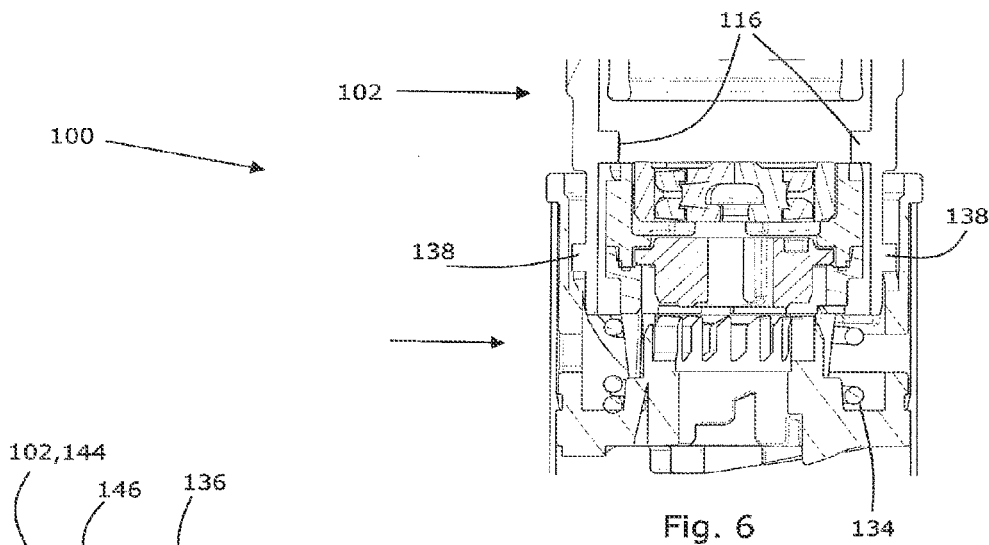
Figure 7:
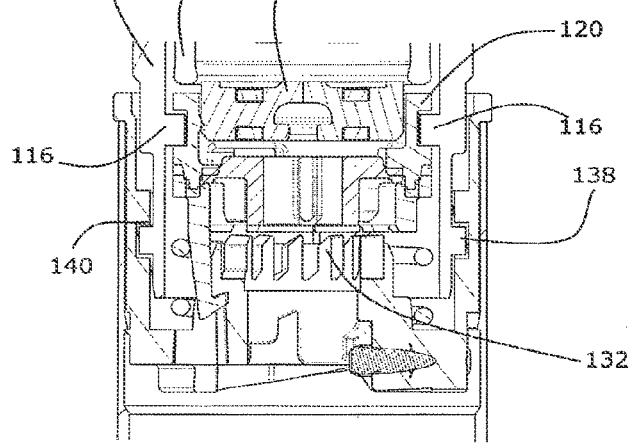
Figure 8:
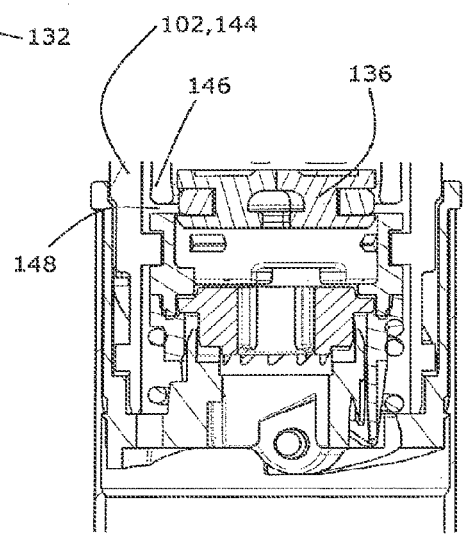

FIGS. 6-8 disclose the fastening process wherein the container 102 is fastened to the dosing assembly 104. Initially the proximal end 110 (cf. FIGS. 1 and 2) of the container 102 is advanced towards the distal end 112 (cf. FIGS. 1 and 2) of the dosing assembly 104. In order to be able to fasten the container 102 to the dosing assembly 104, the container must be rotated until the coding projections 138 of the container 102 are aligned with the coding grooves 140 of the dosing assembly 104. When this is the case, the container 102 may be moved further towards the dosing assembly 104, whereby the fastening projections 106 of the container 102 are received in corresponding fastening grooves 108 of the dosing assembly 104 and the coding projections 138 are received in the coding grooves 140.

Upon further movement, the retaining projections 116 of the container 102 are received in the retaining grooves 118 of the coupling mechanism 120. In FIG. 7 the retaining projections 116 have been advanced into the second part 124 (cf. FIG. 3) of the retaining groove 118 whereby further axial movement of the container 102 in the proximal direction i.e. downwards in the figure, causes the coupling mechanism 120 to be moved in the proximal direction, whereby the teeth 131 of the coupling mechanism 120 engages the teeth 132 of the dosing assembly 104 as described previously.

In the embodiment of FIGS. 6-8, the container 102 comprises a cartridge holder 144 and a glass cartridge 146. The cartridge holder 144 defines the fastening projection 106, the coding projection 138 and the retaining projection 116, and thus the glass cartridge 146 is not used to move the coupling mechanism 120 from the distal position into the proximal position. Accordingly, when the container 102 is fastened to the dosing assembly 104 an air gap 148 is present between the glass cartridge 146 and the coupling mechanism 120. The advantage is that the chain of tolerances between the dosing assembly 104 and the coupling mechanism 120 is only dependent on the tolerances of the fastening projection/groove 106, 108 and the tolerances of the retaining projection/groove 116, 118. Accordingly, the tolerances of the glass cartridge 146 and the cartridge holder 144 are irrelevant. In FIG. 10 a conventional system is illustrated wherein the glass cartridge 146 is used to move the coupling mechanism 120 from the distal position to the proximal end 110. As high tolerances of glass products are expensive to achieve compared to similar tolerances of plastic products, the present invention provides an economic alternative to known systems.

Figures 11, 12:
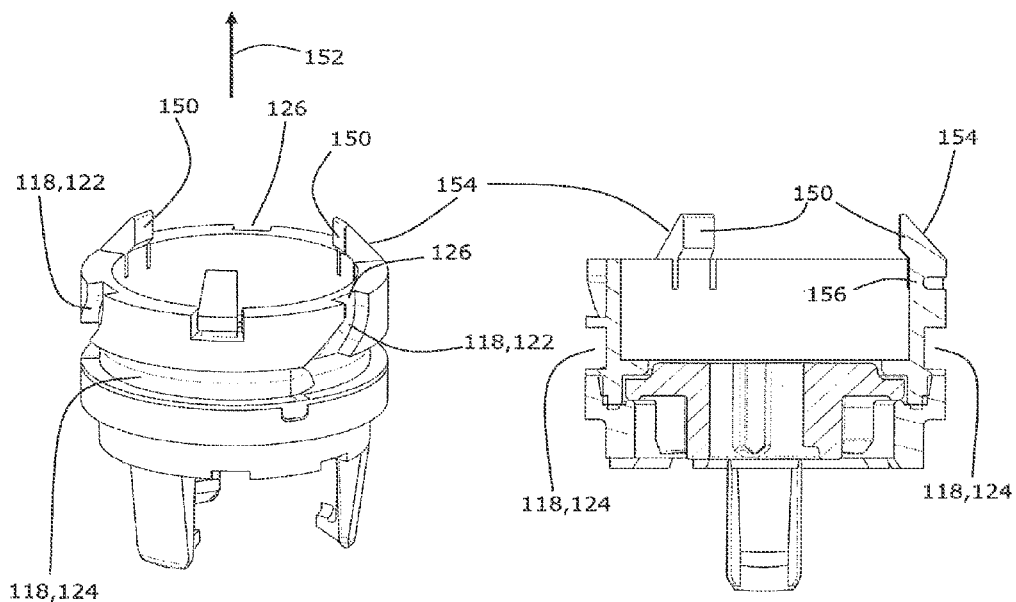
Figure 13:
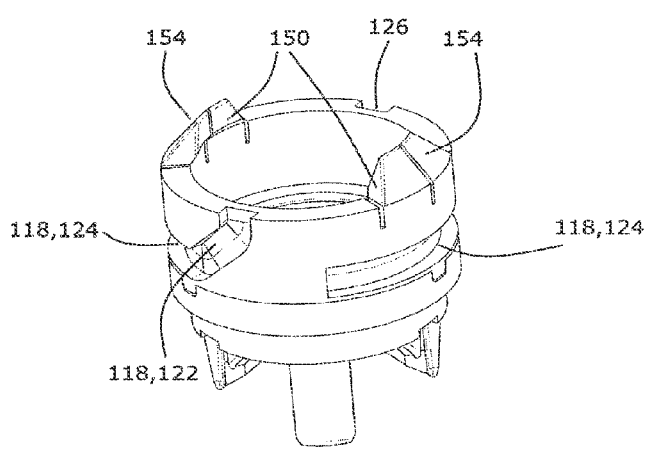

FIGS. 11-13 disclose embodiments of the coupling mechanism 120 having axially extending protrusions 150 bendable between a retaining position wherein the axially extending protrusions 150 prevent a drive stem (not shown) from being moved in the distal direction (i.e. upwards in the drawing), and a non-retaining position (as shown in FIGS. 11-13) wherein the drive stem, when positioned in the initial position is allowed to be moved in the distal direction, as indicated by arrow 152. In the present context, the term "initial position" shall be understood the position in which coupling mechanism 120 encircles the entire drive stem as illustrated in FIG. 6 or wherein the drive stem 136 is positioned proximally relative to the axially extending protrusions 150. The axially extending protrusions 150 define an inclined surface 154 adapted to force the axially extending protrusions 150 towards their retaining position when a glass cartridge is moved axially towards the inclined surface 154 (i.e. in the proximal direction). Accordingly, if the container of FIG. 10 is fastened to a dosing assembly 104 comprising the coupling mechanism 120 of FIGS. 11-13, the drive stem is locked in the initial position and the medicament cannot be expelled. Thus, the present invention provides a system for preventing a wrong medicament from being dispensed by the dosing assembly of the present invention. This improves user safety.

Accordingly, in order for a container to be useable with a dosing assembly 104 comprising the axially extending protrusions 150, the container must be shaped such that when fastened to the dosing assembly, each of the axially extending protrusions is free to move between the retaining and non-retaining position whereby the drive stem, when positioned in the initial position, may be advanced in the distal direction.

Each of the axially extending protrusions 150 defines narrow part 156 defining a bending axis of the axially extending protrusions 150. Accordingly, each of the axially extending protrusions 150 may be bend in the radial direction towards and away from the centre axis of the coupling mechanism 120.

Figure 14:
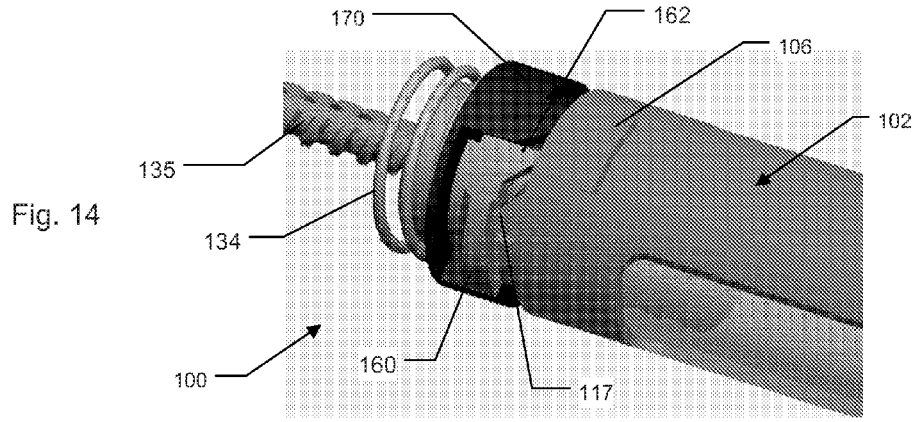
Figure 15:
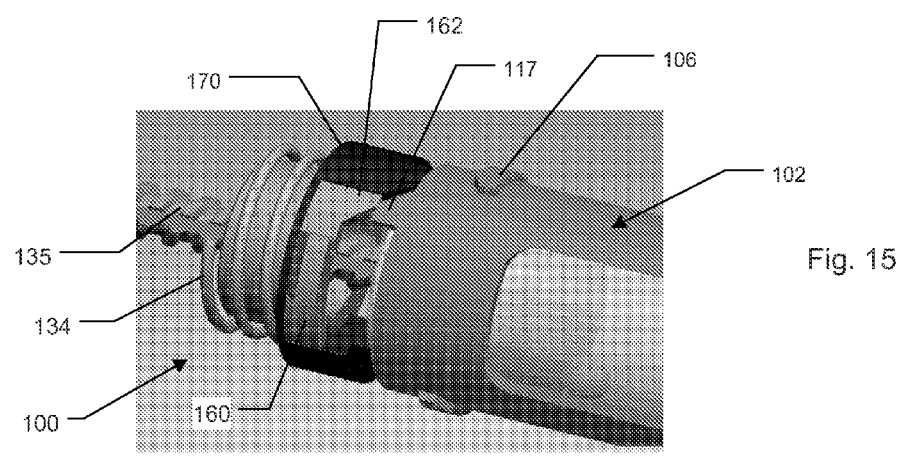
Figure 16:
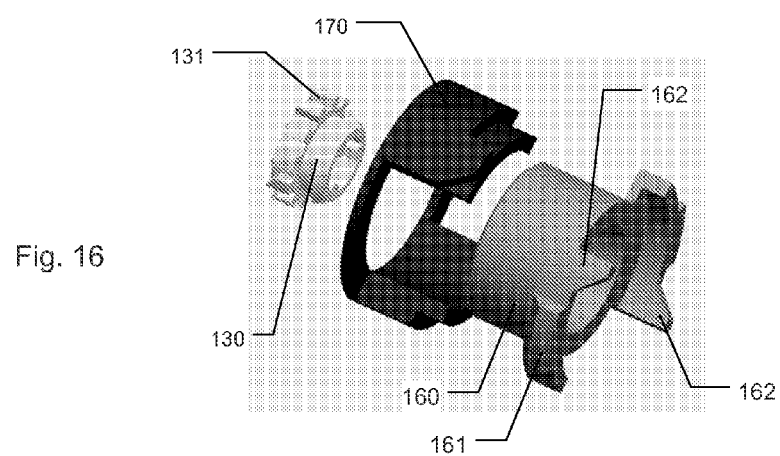

FIGS. 14-16 disclose an embodiment of a medical delivery system where the coupling mechanism is modified to be actuatable by a rotational movement between the container 102 and the dosing assembly. In this embodiment, the fastening procedure for fastening the container to the dosing assembly includes an initial relative axial movement followed by a relative rotational locking movement between container 102 and dosing assembly 104. The fastening projection 106 of container 102 is received in a fastening groove (not shown) of the dosing assembly. The fastening groove of the dosing assembly 104 may be "L"-shaped to provide the above-mentioned fastening procedure.

In FIG. 14, the coupling mechanism comprises an axially moveable pusher member 170 and an axially moveable coupling member 160. Pusher member 170 and coupling member 160 is so shaped that limited relative axial movement is possible, but pusher member 170 is rotationally fixed with respect to coupling member 160. Coupling member 160 comprises radially protrusions 161 adapted to be received in longitudinal tracks (not shown) formed in a housing section of dosing assembly 104. Coupling member 160 is axially moveable between a distal position and a proximal position.

Coupling member 160 accommodates a rotatable guide member 130 (cf. FIG. 16) so that rotatable guide member 130 is free to rotate relative to coupling member 160 but rotatable guide member 130 follows axial movements of coupling member 160.

Rotatable guide member 130 engages and encircle an actuator/piston rod 135 in the same way as disclosed in the embodiment shown referring to aspect 1. Likewise, rotatable guide member 130 includes teeth 131 adapted to engage corresponding teeth of the dosing assembly 104 when the coupling mechanism is positioned in the proximal position. Also, in the embodiment shown in FIGS. 14-16, the pusher member 170 is biased by a spring 134 urging the pusher member 170 towards the distal end. Further biasing means (not visible in FIGS. 14 and 15) urges the coupling member 160 in distal direction.

The container 102 incorporates two inclined surface portions formed as axially protrusions 117 which during rotationally locking of the container 102 to the dosing assembly 104 engages corresponding inclined surface portions 162 formed in coupling member 160.

In the state shown in FIG. 14, the container 102 has been axially moved to abut dosing assembly 104. The pusher member 170, biased by spring 134, exerts a distal force to a cartridge accommodated into a cartridge holder portion of container 102. However, coupling member 160 still remains in its distal position allowing the rotatable guide member 130 to rotate freely with respect to the housing part of the dosing assembly.

In the condition shown in FIG. 15, container 102 has been moved rotationally clockwise with respect to the dosing assembly to properly interlock the two parts. Due to the rotational movement of inclined surfaces 117 with respect to corresponding inclined surfaces 162, the coupling member 160 has been forced into its proximal position whereby rotatable guide member 130 is rotationally locked relative to the hosing section of the dosing assembly. In this state, the drive mechanism of the dosing assembly is able to transfer forces to the actuator/piston rod 135 to move it in the distal direction in accordance with operation of the drive mechanism.

Upon release of the container 102 from the dosing assembly 104 by initially rotating the container in a counter clockwise direction to unlock the two parts, the coupling member 160 is automatically moved in the distal direction allowing the rotatable guide member 130 to spin freely inside the dosing assembly 104. In this state, the resetting of the actuator/piston rod may be carried out by axially displacing the actuator/piston rod 135 in the proximal direction by using a new full container/cartridge 102.

FIG. 16 further depicts additional details of the coupling member 160, the pusher member 170 and the rotatable guide member 130.

Figure 17:
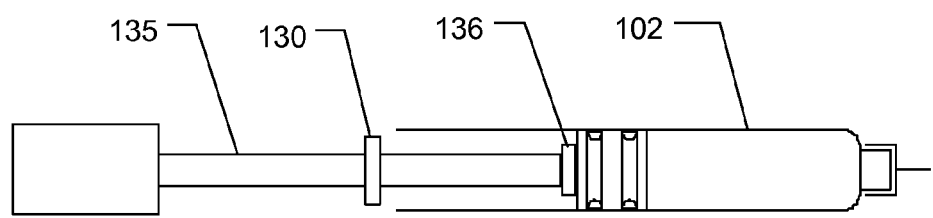
FIG. 17 discloses an embodiment of the invention according to an aspect of the invention.

FIG. 17 further depicts additional details of drive mechanism 180, showing actuator/piston rod 135, guide member 130, drive stem 136, and container 102.

The invention claimed is:

1. A medical delivery system comprising:
 a container adapted to contain a medicament in a chamber defined by the container and a slidably arranged piston which is movable in a distal direction towards an outlet so as to reduce the volume of the chamber and expel the medicament through the outlet;
 a dosing assembly adapted to be fastened to the container and comprising:
  an actuator for advancing the piston in the distal direction,
  a drive mechanism for advancing the actuator in the distal direction, and
  a coupling mechanism movable between a distal position wherein movement of the drive mechanism in the distal direction is not transferred to the actuator, and a proximal position wherein movement of the drive mechanism in the distal direction is transferred to the actuator whereby the piston is moved in the distal direction and the medicament is expelled; and
 wherein one of the container and the dosing assembly defines one or more radially extending fastening projections each of which during fastening of the container to the dosing assembly engages a corresponding radially extending fastening groove of the other one of the dosing assembly and the container whereby the container is fastened to the dosing assembly by an initial axial movement followed by a relative rotational movement;

wherein one of the container and the coupling mechanism defines one or more radially extending retaining projections each of which during fastening of the container to the dosing assembly engages a corresponding radially extending retaining groove of the other one of the coupling mechanism and the container, whereby the coupling mechanism is moved from the distal position to the proximal position as the container is rotated relative to the dosing assembly; and wherein the dosing assembly comprises a rotatable guide member which engages the actuator, the rotatable guide member being either rotationally locked with respect to the actuator or being threadedly engaged with the actuator, and wherein the rotatable guide member is free to rotate in the dosing assembly when the coupling mechanism is in the distal position and wherein the rotatable guide member is rotationally locked in the dosing assembly when the coupling mechanism is in the proximal position.

2. A medical delivery system according to claim 1, wherein, when the container is fastened to the dosing assembly, at least a part of the dosing assembly encircles at least a part of the container, and at least a part of the container encircles at least a part of the coupling mechanism.

3. A medical delivery system according to claim 1, wherein each of the one or more retaining grooves defines a first groove part which, during fastening of the container to the dosing assembly, is adapted to guide the corresponding retaining projection into a second groove part of the retaining groove, the second groove part being shaped so as to allow relative rotational movement between the container and the coupling mechanism.

4. A medical delivery system according to claim 3, wherein the second groove part is shaped such that, when the retaining projection is positioned in the second groove part, translational movement of the container in the proximal direction causes the coupling mechanism to be moved towards the proximal position.

5. A medical delivery system according to claim 3, wherein the second groove part extends circumferentially on an inner or outer surface of the container or coupling mechanism, respectively.

6. A medical delivery system according to claim 5, wherein the fastening groove, the fastening projection, the retaining groove and the retaining projection are arranged with respect to each other, such that upon movement of the fastening projection into an inlet of the fastening groove, the retaining projection is received in an inlet of the retaining groove.

7. A medical delivery system according to claim 1, wherein the actuator is rotatively guided relative to the dosing assembly when the coupling mechanism is positioned in the proximal position, and wherein the actuator is allowed to rotate relative to the dosing assembly when the coupling mechanism is positioned in the distal position.

8. A medical delivery system according to claim 1, wherein the actuator is connected to a drive stem adapted to abut the piston, wherein the drive stem is movable between an initial position and a distal position and wherein the dosing assembly defines one or more axially extending protrusion(s) each of which is movable between a retaining position wherein each of the protrusions retains the drive stem in the initial position and a non-retaining position in which the drive stem, when positioned in the initial position, is allowed to be moved in the distal direction.

9. A medical delivery system according to claim 8, wherein the container is shaped such that when fastened to the dosing assembly, each of the axially extending protrusions is allowed to move between the retaining and non-retaining position whereby the drive stem, when positioned in the initial position, may be advanced in the distal direction.

10. A medical delivery system according to claim 1, wherein the container comprises:
a first container adapted to be fastened to a first dosing assembly according to any of the preceding claims; and
a second container adapted to be fastened to a second dosing assembly according to any of the preceding claims; and wherein at least one of the retaining groove, the retaining projection, the fastening groove and the fastening projection is/are adapted to prevent the first dosing assembly and second container from being fastened to each other, and to prevent the second dosing assembly and the first container from being fastened to each other.

11. A container for use in the medical delivery system according to claim 1, the container comprising at least one fastening projection extending in a radial direction from an outer surface the container, and at least one retaining projection extending in a radial direction from an inner surface of the container.

12. A dosing assembly for use in the medical delivery system according to claim 1, comprising an actuator movable in a distal direction, a drive mechanism for advancing the actuator on the distal direction and a coupling mechanism movable between a distal position wherein movement of the drive mechanism in the distal direction is not transferred to the actuator, and a proximal position wherein movement of the drive mechanism in the distal direction is transferred to the actuator, and wherein
a retaining groove is defined on an outer circumferential surface of the coupling mechanism, and
a fastening groove is defined on an inner surface of the dosing assembly.

13. A medical delivery system comprising:
a container adapted to contain a medicament in a chamber defined by the container and a slidably arranged piston which is movable in a distal direction towards an outlet so as to reduce the volume of the chamber and expel the medicament through the outlet;
a dosing assembly adapted to be fastened to the container and comprising:
an actuator for advancing the piston in the distal direction,
a drive mechanism for advancing the actuator in the distal direction, and
a coupling mechanism including a rotatable guide member which engages the actuator, the rotatable guide member being either rotationally locked with respect to the actuator or being threadedly engaged with the actuator, the coupling mechanism being movable between a distal position wherein the rotatable guide member is free to rotate in the dosing assembly and wherein movement of the drive mechanism in the distal direction is not transferred to the actuator and a proximal position wherein the rotatable guide member is rotationally locked in the dosing assembly and wherein movement of the drive mechanism in the distal direction is transferred to the actuator whereby the piston is moved in the distal direction and the medicament is expelled; and wherein one of the container and the dosing assembly defines one or more radially extending fastening projections each of which during fastening of the container to the dosing assembly engages a corresponding radially extending fastening groove of the other one of the dosing assembly and the container whereby the container is fastened to the dosing assembly, the fastening projections and grooves being adapted to fasten the container to the dosing assembly by a relative translational movement along an axis followed by a relative rotational locking movement around the axis; and wherein one of the container and the coupling mechanism comprises an inclined surface portion adapted to engage upon said relative locking movement an engagement surface of the other of the container and the coupling mechanism, the inclined surface portion being arranged to move the coupling mechanism from the distal position to the proximal position upon said relative rotational locking movement.

14. A medical delivery system comprising:

a container adapted to contain a medicament in a chamber defined by the container and a slidably arranged piston which is movable in a distal direction towards an outlet so as to reduce the volume of the chamber and expel the medicament through the outlet;

a dosing assembly adapted to be fastened to the container and comprising:
  an actuator for advancing the piston in the distal direction,
  a rotatable guide member which engages the actuator, the rotatable guide member being either rotationally locked with respect to the actuator or being threadedly engaged with the actuator,
  a drive mechanism for advancing the actuator in the distal direction, and
  a coupling mechanism comprising an axially movable coupling member adapted to cooperate with the rotatable guide member, the axially movable coupling member being movable between a distal position wherein the rotatable guide member is free to rotate in the dosing assembly and wherein movement of the drive mechanism in the distal direction is not transferred to the actuator and a proximal position wherein the rotatable guide member is rotationally locked in the dosing assembly and wherein movement of the drive mechanism in the distal direction is transferred to the actuator whereby the piston is moved in the distal direction and the medicament is expelled; and wherein one of the container and the dosing assembly defines one or more radially extending fastening projections each of which during fastening of the container to the dosing assembly engages a corresponding radially extending fastening groove of the other one of the dosing assembly and the container whereby the container is fastened to the dosing assembly, the fastening projections and grooves being adapted to fasten the container to the dosing assembly by a relative translational movement along an axis followed by a relative rotational locking movement around the axis; and wherein one of the container and the coupling mechanism comprises an inclined surface portion adapted to engage upon said relative locking movement an engagement surface of the other of the container and the coupling mechanism, the inclined surface portion being arranged to move the coupling mechanism from the distal position to the proximal position upon said relative rotational locking movement.

* * * * *

UNITED STATES PATENT AND TRADEMARK OFFICE
CERTIFICATE OF CORRECTION

Page 1 of 1

PATENT NO. : 8,740,857 B2
APPLICATION NO. : 12/518502
DATED : June 3, 2014
INVENTOR(S) : Christiansen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1011 days.

Signed and Sealed this
Eighth Day of September, 2015

Michelle K. Lee
*Director of the United States Patent and Trademark Office*